(12) United States Patent
Da Costa Martins et al.

(10) Patent No.: US 8,367,342 B2
(45) Date of Patent: Feb. 5, 2013

(54) CARDIAC HYPERTROPHY

(75) Inventors: Paula Alexandra Da Costa Martins, Utrecht (NL); Leon Johannes De Windt, Culemborg (NL)

(73) Assignee: Lead Pharma Drug Development IP B.V., Graafseweg (NL)

( * ) Notice: Subject to any disclaimer, the term of this patent is extended or adjusted under 35 U.S.C. 154(b) by 552 days.

(21) Appl. No.: 12/520,516

(22) PCT Filed: Dec. 19, 2007

(86) PCT No.: PCT/NL2007/050673
§ 371 (c)(1),
(2), (4) Date: Nov. 5, 2009

(87) PCT Pub. No.: WO2008/078998
PCT Pub. Date: Jul. 3, 2008

(65) Prior Publication Data
US 2010/0055732 A1   Mar. 4, 2010

(30) Foreign Application Priority Data
Dec. 22, 2006  (EP) .................................. 06077242

(51) Int. Cl.
*C12Q 1/68*  (2006.01)

(52) U.S. Cl. ...................................................... 435/6.13
(58) Field of Classification Search .................. None
See application file for complete search history.

(56) References Cited

PUBLICATIONS

Zhao et al. Nature 2005, vol. 436, pp. 214-220.*
Fernandez-Teran et al., Development (2000) 127:2133-2142.
Howard et al., Development (2000) 127:4073-4081.
International Search Report for PCT/NL2007/050673, mailed on Apr. 4, 2008, 4 pages.
McFadden et al., Development and Disease (2005) 132:189-201.
Russell et al., Biochimica Et Biophysica Acta (1998) 1443:393-399.
Togi et al., Molecular and Cellular Biology (2004) 24 (11):4627-4635.
Yamagishi et al., Science (1999) 283:1158-1161.
Kelly et al., "Cell history determines the maintenance of transciptional differences between left and right ventricular cardiomyocytes in the developing mouse heart," Journal of Cell Science (2003) Journal of Cell Science 116:5005-5013.

* cited by examiner

*Primary Examiner* — Tracy Vivlemore
(74) *Attorney, Agent, or Firm* — Morrison & Foerster LLP

(57) ABSTRACT

The invention provides means and methods for at least in part inducing, counteracting, preventing and/or investigating cardiac hypertrophy.

8 Claims, 6 Drawing Sheets

CARDIAC HYPERTROPHY

CROSS-REFERENCE TO RELATED APPLICATIONS

This application is the national phase of PCT application PCT/NL2007/050673 having an international filing date of 19 Dec. 2007, which claims benefit of European application No. 06077242.3 filed 22 Dec. 2006. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(A), is incorporated herein by reference in its entirety for all purposes. The sequence listing is identified on the electronically filed text file as follows:

| File Name | Date of Creation | Size (bytes) |
| --- | --- | --- |
| 313632006800Seqlist.txt | May 14, 2012 | 601 bytes |

The invention relates to the fields of biology and medicine. More particularly, the invention relates to cardiac disorders.

Cardiac disorders are a major cause of mortality worldwide. Heart failure is one of the commonly occurring cardiac disorders. Heart failure (HF), or the inability of the heart to meet hemodynamic demands, is regarded as the end-stage of various forms of cardiac disease. Despite significant progress in the prevention and treatment of cardiovascular disease in the United States in the past two decades, statistics indicate that the incidence and prevalence of heart failure have been increasing steadily, especially in the elderly. Chronic heart failure affects 4.8 million Americans and is the leading cause of hospitalization for people aged 65 years and over. Despite improved medical treatment and intense investigation, heart failure is a leading cause of morbidity and mortality in industrial countries. In the Western world, the prevalence and incidence of HF are increasing steadily. HF is now the leading cause of hospitalization in the elderly. Survival after the onset of HF is grim, with a 5-year survival rate as low as 25% in men and 38% in women.

The leading causes of HF are cardiac ischemic disease and hypertensive heart disease. In both pathologies, left ventricular hypertrophy (LVH) plays an important role. LVH develops in response to increased biomechanical stress resulting from various conditions. Firstly, long-term pressure overload results from hypertension, aortic stenosis or coarctation of the aorta. Secondly, surviving myocardium after myocardial infarction faces an increased diastolic wall stress. Thirdly, defects in genes encoding sarcomeric, cytoskeletal or mitochondrial proteins result in myocardial incompetence to meet output demands. LVH was conventionally conceptualized to be required to maintain LV function by normalizing wall stress, as dictated by the law of Laplace. With disease progression, LVH would in some cases progress to maladaptive LVH, characterized by increased fibrosis, which leads the way to HF. The concept of adaptive and maladaptive LVH is now being challenged by data from animal experimental research, suggesting that any degree of LVH is detrimental for LV function and survival. In addition, observational studies have demonstrated that increased LV mass is associated with reduced LV function, and that LV dysfunction ameliorates upon LVH regression.

Sustained LVH has been recognized as the single most important risk factor for heart failure development, at least in conditions with increased load such as chronic hypertension or valvular disease, and a powerful predictor for cardiovascular morbidity and mortality.

Currently, heart failure is induced in experimental animals by inducing biomechanical stress (for instance aortic banding). Alternatively, compounds known to induce heart failure are used. Limited information is however available about the biological pathways involved with heart failure.

There is a need in the art for alternative methods for generating (model systems for) cardiac hypertrophy. Furthermore, there is a need for methods for identifying and developing therapeutic compounds capable of counteracting cardiac hypertrophy. Methods for influencing cardiac hypertrophy, in vitro as well as in vivo, are also desired.

The invention provides the insight that the transcription factor Heart and Neural Crest Derived 2 (HAND2) is involved with cardiac hypertrophy. Cardiac hypertrophy is defined herein as enlargement of the size of a heart muscle cell above its natural size in a healthy situation. During cardiac hypertrophy, the mean size of the heart muscle cells is at least 15%, preferably at least 20%, more preferably at least 30% larger than the mean size of heart muscle cells in a healthy individual. The size of a cell is for instance measured by determining its dimensions. Alternatively, cardiac hypertrophy is measured by determining the weight of (at least part of) a heart and comparing said weight with the weight of (the same part of) a heart in a healthy individual. Cardiac hypertrophy often impedes the healthy status of the heart. Hypertrophy of heart muscle cells often results in heart disorders.

A heart muscle cell, also called a cardiac muscle cell or a cardiomyocyte, is a cell similar to, originating from, or derived of a muscle cell which in a natural situation is present in the heart of a vertebrate organism. Said cell need not be directly obtained from heart tissue since it is also possible to culture and/or store this kind of cell in vitro.

HAND2 is a transcription factor which is a member of the family of basic helix-loop-helix transcription factors. HAND2 is expressed during the embryonic phase, where it plays a role in heart development. In normal adult myocardium, HAND2 is expressed at very low levels. The proximal promoter of HAND2 comprises three Nuclear Factor of Activated T-cells (NFAT) consensus binding sites.

According to the present invention, (over)expression of HAND2, and/or an increased activity of HAND2, results in cardiomyocyte hypertrophy. Hence, it has become possible to influence the extent of cardiac hypertrophy by influencing, directly or indirectly, the amount and/or activity of HAND2 in a cardiomyocyte. Moreover, the invention provides a wide variety of applications wherein cells expressing HAND2 or a HAND2-like compound are used. For instance, cells which express HAND2 or a HAND2-like compound are particularly suitable for identifying compounds capable of influencing cardiac hypertrophy. Influencing the HAND2 expression and/or activity in non-human animals is also useful, for instance for therapeutical, research and screening purposes.

One aspect of the present invention provides a method for influencing cardiac hypertrophy, comprising influencing the amount and/or activity of HAND2 in a cardiomyocyte. In one embodiment cardiac hypertrophy is induced and/or enhanced by increasing the amount and/or activity of HAND2. In another embodiment cardiac hypertrophy is counteracted and/or prevented by reducing the amount and/or activity of HAND2. Cardiac hypertrophy is preferably prevented by preventing the presence and/or activity of HAND2. The presence, amount and/or activity of HAND2 is either directly or indirectly influenced. Directly influencing the amount and/or activity of HAND2 is for instance performed using a compound capable of binding HAND2 or a compound capable of binding a nucleic acid sequence encoding HAND2 or any regulatory sequence thereof. Indirectly influencing the amount and/or activity of HAND2 for instance comprises the use of a first compound capable of binding a second compound, and/or the use of a first compound capable of binding a nucleic acid sequence encoding a second compound, wherein said second compound is capable of influencing the amount, expression and/or activity of HAND2. Hence, in such case, by influencing the amount and/or activity of said second compound, the amount and/or activity of HAND2 is indirectly influenced as well.

One embodiment comprises influencing the expression of HAND2 or a functional part, derivative and/or analogue thereof. In another embodiment, the activity of HAND2 or a functional part, derivative and/or analogue thereof is influenced, for instance using a binding molecule.

In one preferred embodiment of the present invention the amount and/or activity of HAND2 or a HAND2-like compound in a cell is increased. If the amount and/or activity of HAND2 or a HAND2-like compound is increased in a cardiomyocyte, cardiac hypertrophy is induced and/or enhanced. The resulting cell, having an increased size, is for instance suitable for studying the implications and effects of cardiac hypertrophy. Moreover, a cell wherein the amount and/or activity of HAND2 or a HAND2-like compound is increased is particularly suitable for testing whether a candidate compound is capable of counteracting cell hypertrophy. The effect of a candidate compound is not necessarily investigated with a cardiomyocyte. Any cell comprising HAND2 or a HAND2-like compound is suitable.

The invention provides an isolated or recombinant cell wherein expression, the amount and/or the activity of heart and neural crest derived 2 (HAND2) or a functional part, derivative and/or analogue of HAND2 is increased as compared to the same kind of cell in its natural environment.

An increased expression, amount and/or activity of HAND2 as compared to the same kind of cell in its natural environment means herein that the expression, amount and/or activity of HAND2 is increased as compared to the natural, healthy situation in vivo. For instance, mature cardiac muscle cells of a healthy individual barely express HAND2. An isolated or recombinant mature cardiac cell according to the present invention however comprises an amount and/or activity of HAND2 which is larger than the natural variation between cardiac cells of said healthy individual.

Expression, amount and/or activity of HAND2 is increased in a variety of ways. In one embodiment, a cell of interest is provided with a nucleic acid sequence encoding HAND2 or a functional part, derivative and/or analogue thereof. Expression of said nucleic acid in said cell results in an increased amount of HAND2 or HAND2-like compound. An isolated or recombinant cell comprising an exogenous nucleic acid sequence encoding heart and neural crest derived 2 (HAND2) or a functional part, derivative and/or analogue of HAND2 is therefore also herewith provided, as well as a use of a nucleic acid sequence encoding HAND2 or a functional part, derivative and/or analogue thereof for transfecting a cell of interest.

As used herein, the term "nucleic acid sequence" also encompasses non-natural sequences based on and/or derived from nucleic acid sequences, such as for instance artificially modified nucleic acid sequences, peptide nucleic acids, as well as nucleic acid sequences comprising at least one modified nucleotide and/or non-natural nucleotide such as for instance inosine.

A functional part of HAND2 is defined as a part of HAND2 which is capable of inducing and/or enhancing cardiac hypertrophy. A functional part of HAND2 is for instance provided by generating a proteinaceous molecule comprising a HAND2 sequence wherein at least one amino acid residue which is not essential for promoting cardiac hypertrophy has been omitted. A functional part preferably has a length of at least 70%, preferably at least 80% of the length of wild type HAND2. Said functional part preferably has a length of between 5 and 25 kD, preferably between 10 and 21 kD.

A functional derivative of HAND2 is defined as an HAND2 molecule which has been altered such that the cardiac hypertrophy inducing property of the resulting compound is essentially the same in kind, albeit not necessarily in amount. A derivative of HAND2 is a compound with an amino acid sequence which is at least 70%, preferably at least 75%, more preferably at least 80%, more preferably at least 85%, most preferably at least 95% homologous to an HAND2 amino acid sequence. A derivative of HAND2 is provided in many ways, for instance through conservative amino acid substitution, whereby an amino acid residue is substituted by another residue with generally similar properties (size, hydrophobicity, etc), such that the overall functioning is likely not to be seriously affected.

A person skilled in the art is well able to generate analogous compounds of HAND2. This is for instance done through screening of a peptide library. Such an analogue has essentially the same cardiac hypertrophy inducing/enhancing property as HAND2 in kind, not necessarily in amount.

As used herein, the terms "HAND2" and "HAND2-like compound" also mean a functional part, derivative and/or analogue of HAND2.

The amount and/or activity of HAND2 is increased in a variety of alternative ways. In one embodiment a cell is provided with a compound capable of increasing the expression and/or activity of HAND2. Such compound is preferably administered to a cell in order to increase the expression and/or activity of endogenous HAND2. Additionally, or alternatively, such compound is administered to a cell in order to increase the expression and/or activity of exogenous HAND2 or a functional part, derivative and/or analogue thereof, which is encoded by an exogenous nucleic acid sequence present in said cell. Compounds capable of increasing expression and/or activity of HAND2 are known in the art. Non limiting examples include NFAT activity enhancers such as for instance, but not limited to, cardiotrophin-1, phenylephrine, norepinephrin and endothelin-1.

In another preferred embodiment, a cell is provided with a nucleic acid sequence capable of directly or indirectly increasing HAND2 expression and/or HAND2 activity. As a result, the amount and/or activity of HAND2 or HAND2-like compound in said cell is increased, resulting in hypertrophy in case of a cardiomyocyte. An isolated or recombinant cell comprising an exogenous nucleic acid sequence capable of directly or indirectly increasing HAND2 expression and/or activity is therefore also provided. Said exogenous nucleic acid sequence is preferably capable of increasing endogenous HAND2 expression or activity, thereby obviating the need of providing said cell with a second exogenous nucleic acid encoding HAND2 or a HAND2-like compound. In one preferred embodiment a cell is provided with a nucleic acid sequence encoding a proteinaceous molecule capable of increasing (endogenous) HAND2 expression or activity, such as for instance calcineurin and/or NFAT.

A cell with an altered amount and/or activity of HAND2 or HAND2-like compound is suitable for a wide variety of applications. For instance, a cardiomyocyte with an increased amount and/or activity of HAND2 or a HAND2-like compound is suitable for investigating the effects of cardiac hypertrophy. Cells comprising HAND2 and/or a HAND2-like compound are also suitable for screening for possible therapeutic compounds. Any kind of cell comprising HAND2 and/or a HAND2-like compound is suitable for this purpose. Preferably, a cell overexpressing HAND2 or a HAND2-like compound is used.

The desired amount and/or activity of HAND2 in a cell according to the invention is dependent on a particular situation. In some situations, for instance during testing of candidate compounds, a higher amount and/or activity of HAND2 is desired than in other situations, such as for instance during culturing. Therefore, expression of HAND2 or a functional part, derivative and/or analogue thereof is preferably inducible, so that the extent of expression can be varied at will and, preferably, induced when required. Further provided is therefore a cell according to the invention, wherein expression of HAND2 or a functional part, derivative and/or analogue thereof is inducible.

Inducible expression systems are well known in the art. Non limiting examples comprise: 1) RheoSwitch Mammalian Inducible Expression Systems, activatable by synthetic ligands such as RSL1 or homologues thereof (Kumar et al. (2004) *J. Biol. Chem.*; 279: 27211); 2) ecdysone-inducible promoter systems, activatable by insect moulting hormones (ecdysone and its homologues), generally called ecdysteroids (Karzenowski et al. Biotechniques 2005; 39:191); 3) tetracycline-inducible or tetracycline-repressive systems in combination with tetracyclin (or derivates thereof) (van de Wetering et al. Cell 2002; 111:241); 4) heat-shock inducible promoter systems (Siddiqui et al. Int J hyperthermia 2006:22:587); and 5) tamoxifen-inducible systems by creating a fusion of the target with (parts of) the estrogen receptor, activatable by tamoxifen or estrogen related homologues (Sohal et al. Circ Res 2001:89:20).

Alternatively, HAND2 or a functional part, derivative and/or analogue thereof is constitutively overexpressed, for instance by placing a nucleic acid sequence encoding HAND2 or a functional part, derivative and/or analogue thereof under control of a ubiquitous or organ-specific promoter.

If a cell according to the invention is provided with an exogenous nucleic acid sequence, a readout system is preferably incorporated as well. With such readout system it is easily determined whether a cell has been successfully transfected. Readout systems are well known in the art. Non limiting examples of well known suitable readout systems comprise 1) luminescent or fluorescent reporters such as for instance luciferase (renilla, firefly) or green fluorescent protein (GFP) or homologues thereof (EYFPm DsRed2, ECFP); and 2) enzyme reporters such as for instance beta-galactosidase (LacZ), secreted alkaline phosphatase (SEAP), chloramphenicol acetyltransferase (CAT). Further provided is therefore an isolated or recombinant cell according to the invention further comprising a readout system.

A cell provided by the present invention comprises any cell wherein the amount and/or activity of HAND2, or a functional part, derivative and/or analogue thereof, is altered as compared to the natural situation of the same kind of cell. Said cell preferably comprises a myocyte or a precursor thereof. More preferably, said cell comprises a cardiomyocyte. In vivo, hypertrophy of cardiomyocytes results in cardiomyopathy, a disorder of heart muscle. Cardiomyocytes according to the present invention are therefore particularly suitable for investigating cardiomyopathy and possible therapeutic applications. In a particularly preferred embodiment a cell according to the present invention comprises a cardiomyocyte progenitor cell and/or stem cell. If an exogenous nucleic acid sequence is stably integrated in the genome of a cardiomyocyte progenitor cell or stem cell, culturing of such cell results in development of cardiomyocytes which also comprise said exogenous nucleic acid. Transfection of a single progenitor cell or stem cell thus yields a plurality of modified differentiated cells. The use of progenitor cells and/or stem cells is therefore preferred.

One further embodiment provides a cell according to the invention, wherein a nucleic acid sequence encoding HAND2 or a functional part, derivative and/or analogue thereof is operably linked to an exogenous regulatory element which is specific for myocardial cells. Said exogenous regulatory element is for instance operably linked with an endogenous HAND2 gene in order to enhance expression of said gene and/or to render expression of said endogenous HAND2 gene inducible in myocardial cells. Alternatively, or additionally, said exogenous regulatory element is operably linked with an exogenous nucleic acid sequence encoding HAND2 or a functional part, derivative and/or analogue thereof. The use of an exogenous regulatory element which is specific for myocardial cells provides various advantages. For instance, if stem cells and/or progenitor cells are transduced, HAND2 will not be (over)expressed in all kinds of differentiated cells but mainly in myocardial cells, facilitating enrichment and/or isolation of myocardial cells.

One aspect of the present invention provides a non-human animal wherein the amount and/or activity of HAND2 or a HAND2-like compound is increased as compared to the same kind of animal in a natural, healthy situation. Said non human animal preferably comprises a cell according to the present invention. If the amount and/or activity of HAND2 or a functional part, derivative and/or analogue thereof is increased in cardiomyocytes of a non human animal, cardiac hypertrophy is induced in vivo. This way, it is possible to investigate (pathogenic) effects of cardiac hypertrophy. Moreover, a non human animal expressing HAND2 or a HAND2-like compound is suitable for screening for compounds capable of at least in part counteracting the amount and/or activity of HAND2, preferably for compounds capable of counteracting cardiac hypertrophy. One preferred embodiment provides a non-human animal comprising an exogenous nucleic acid sequence encoding HAND2 or a functional part, derivative and/or analogue thereof. Expression of such exogenous nucleic acid sequence results in an increased amount and/or activity of HAND2 or HAND2-like compound.

A non-human animal according to the invention preferably comprises a nucleic acid sequence encoding HAND2 or a functional part, derivative and/or analogue thereof, which nucleic acid sequence is operably linked to an exogenous regulatory element which is inducible. Said inducible exogenous regulatory element is preferably operably linked to an endogenous HAND2 gene. This way, expression of endogenous HAND2 is regulated at will. Alternatively, or additionally, a non human animal according to the invention is provided which comprises an exogenous nucleic acid sequence encoding HAND2, or a functional part, derivative and/or analogue thereof, operably linked to an exogenous regulatory element which is inducible. This way, expression of exogenous HAND2 is regulated at will. As described hereinbefore, various inducible expression systems are well known in the art.

One embodiment provides a non human animal comprising a nucleic acid sequence encoding HAND2 or a functional part, derivative and/or analogue thereof, operably linked to an exogenous regulatory element which is specific for myocardial cells. This way, HAND2 or a functional part, derivative and/or analogue thereof will mainly be overexpressed in the animal's myocardial cells. Such animal will therefore suffer from cardiomyopathy, while other functions will be barely, if at all, affected. Such animal is therefore particularly suitable for investigating (effects of) cardiomyopathy, (candidate) therapeutically active compounds and therapies.

In some situations such as for instance when comparative tests are performed in order to determine the efficacy of a HAND2 inhibitory compound it is preferred to diminish expression of endogenous HAND2 in a non human animal. More preferably, expression of endogenous HAND2 is essentially inhibited. Expression of endogenous HAND2 is diminished or inhibited in various ways known in the art. For instance, an endogenous HAND2 gene is at least in part deleted and/or substituted via homologous recombination. Preferably, endogenous HAND2 is exchanged for an antibiotic resistance gene or a reporter gene such as, but not limited to, beta-galactosidase. In another embodiment an endogenous HAND2 gene is rendered inactive, for instance via site directed mutagenesis resulting in an inactive gene or by administration of a nucleic acid molecule comprising an antisense sequence such as for instance small interfering RNA (siRNA). In one preferred embodiment Cre-loxP and/or Flp-Frt technology is used.

Further provided is therefore a non-human animal whose endogenous HAND2 gene is at least in part deleted and/or silenced.

A non human animal according to the present invention preferably comprises a mammal, for instance a rodent such as, but not limited to, a rat, a mouse, a guinea pig or a rabbit. In one embodiment said non human animal comprises a pig or a monkey since the biological functions of these animals are particularly well comparable to biological functions of humans.

One preferred application of a cell and/or non human animal comprising HAND2 and/or a HAND2-like compound is a screening method for therapeutically effective compounds. Such cells are for instance suitable for screening for a compound capable of counteracting the amount and/or activity of HAND2 or a HAND2-like compound. In one embodiment cell hypertrophy is induced and/or enhanced by increasing the amount and/or activity of HAND2 or a HAND2-like compound in a cardiomyocyte. Such cell is particularly suitable for investigating whether a candidate compound is capable of counteracting cardiac hypertrophy. Alternatively, or additionally, it is investigated whether a candidate compound is capable of at least in part preventing cell hypertrophy. In one embodiment said screening method is performed in vitro, using an isolated or recombinant cell according to the present invention. In another embodiment said screening method is performed in vivo, using a non human animal according to the present invention. A use of an isolated or recombinant cell according to the invention or a non human animal according to the invention in order to determine whether a candidate compound is capable of counteracting cell hypertrophy is therefore also herewith provided.

In one embodiment possible therapeutic activity of a candidate compound is for instance investigated using at least two in vitro cultures comprising cells which express HAND2 or a functional part, derivative and/or analogue thereof. Preferably the same kind of cells is used in each culture. A candidate compound is administered to at least one culture, whereas at least one other culture is unmodified and functions as a control. Besides the presence or absence of a candidate compound, similar culture conditions are preferably maintained in all cultures. In one embodiment it is determined, after incubation with said candidate compound, whether cells in a culture comprising a candidate compound express significant less HAND2 and/or HAND2-like compound as compared to cells in a culture without said candidate compound. In that case, said candidate compound is capable of counteracting HAND2 expression. This indicates that such candidate compound is capable of at least in part counteracting and/or preventing cardiac hypertrophy. In one embodiment in vitro cultures comprising cardiomyocytes expressing HAND2 or a functional part, derivative and/or analogue thereof are used. A candidate compound is administered to at least one culture, whereas at least one other culture is unmodified and functions as a control. Besides the presence or absence of a candidate compound, similar culture conditions are preferably maintained in all cultures. Subsequently, after incubation with said candidate compound, it is preferably determined whether the (mean) size of the cardiomyocytes in a culture comprising a candidate compound is smaller than the (mean) size of cardiomyocytes cultured in the absence of said candidate compound. If this is the case, it shows that said candidate compound is capable of counteracting cardiomyocyte hypertrophy. Provided is thus a method for determining whether a candidate compound is capable of counteracting cardiac hypertrophy, comprising:

culturing an HAND2 or HAND2-like compound expressing cardiomyocyte in the presence of said candidate compound; and determining whether the size of said cardiomyocyte is smaller than the size of a cardiomyocyte cultured in the absence of said candidate compound.

Preferably, cells according to the invention are cultured in the presence of a candidate compound during at least 12 hours, preferably during at least 24 hours. It is preferably determined after at least 12 hours whether a cell cultured in the presence of a candidate compound expresses lower amounts of HAND2 or a HAND2-like compound as compared to the same kind of cell cultured without said candidate compound. If hypertrophic cardiomyocytes are used, it is preferably determined after at least 12 hours whether the (mean) size of said cardiomyocytes is smaller than the (mean) size of cardiomyocytes cultured in the absence of said candidate compound. Most preferably, this is assessed within a time frame of between 24 hours and 96 hours.

In one embodiment hypertrophy of cardiomyocytes has been induced before said candidate compound is administered to the cells. This is however not necessary: it is also possible to administer a candidate compound to HAND2 or HAND2-like compound expressing cardiomyocytes before cell hypertrophy has been induced. In this embodiment it is determined whether a candidate compound is capable of at least in part preventing the development of cell hypertrophy. In another embodiment, a candidate compound is administered to HAND2 or HAND2-like compound expressing cells other than cardiomyocytes, such as for instance fibroblasts and/or tumor cells. It is for instance determined whether said candidate compound is capable of counteracting and/or inhibiting HAND2 expression in said cell. If this is the case, it indicates that said candidate is capable of counteracting hypertrophy of cardiac muscle cells. Hence, cells other than cardiomyocytes, which cells express HAND2 and/or HAND2-like compound, are suitable for determining whether a candidate compound is capable of counteracting or at least in part preventing cardiac muscle cell hypertrophy.

Once cardiac muscle cell hypertrophy has been established by inducing and/or enhancing HAND2 expression, it is preferably determined whether the (mean) size of said cells reduces over time in the presence of a candidate compound. In this embodiment, it is determined whether the size of a HAND2 expressing cardiac muscle cell has become smaller after incubation with a candidate compound, as compared to the size of said cell before said candidate compound was administered. If this is the case, the candidate compound is capable of counteracting cardiac hypertrophy. Such compound is therefore particularly suitable for treating cardiac hypertrophy related disorders. Further provided is therefore a method for determining whether a candidate compound is capable of counteracting cardiac hypertrophy, comprising:

culturing an HAND2 and/or HAND2-like compound expressing cardiomyocyte which exhibits hypertrophy in the presence of said candidate compound; and determining whether the size of said cardiomyocyte reduces over time.

A method according to the invention is preferably performed with a cell according to the invention. This is however not necessary: it is also possible to use cells which naturally exhibit a significant HAND2 expression, such as for instance embryonic cardiomyocytes.

It is of course also possible to screen candidate compounds with non human animals which express HAND2 and/or a HAND2-like compound. This is preferably performed once a promising candidate compound has been selected with an in vitro method according to the present invention wherein a cell culture was used. In one embodiment the effect of a candidate compound on the occurrence of cardiomyocyte hypertrophy is established in order to determine whether said candidate compound is capable of influencing, at least in part preventing and/or counteracting cardiac hypertrophy. One embodiment provides a method for determining whether a candidate compound is capable of counteracting and/or at least in part preventing cardiac hypertrophy, comprising:

providing an HAND2 and/or HAND2-like compound expressing, non human animal, which exhibits cardiac hypertrophy, with said candidate compound; and determining whether the size of the enlarged cells of said non human animal decreases over time.

Said cells preferably comprise cardiomyocytes. Preferably a non human animal according to the invention exhibiting hypertrophy of cardiomyocytes is used, because such animal is suffering from, or at risk of suffering from, cardiomyopathy. A candidate compound capable of at least in part preventing or counteracting cardiomyocyte hypertrophy is thus a promising candidate for anti cardiomyopathy therapy.

A non human animal comprising HAND2 expressing cells and/or HAND2-like compound expressing cells other than cardiomyocytes is also suitable for a method according to the invention. Such animal is preferably used for determining whether a candidate compound is capable of counteracting expression of HAND2 or a HAND2-like compound.

Preferably, a non human animal according to the invention comprising a HAND2 encoding nucleic acid sequence, and/or a HAND2-like compound encoding nucleic acid sequence, under control of an inducible regulatory element is used so that HAND2 expression is regulated at will. In one embodiment HAND2 expression by cardiomyocytes is not induced nor enhanced until said animal is provided with a candidate compound. In this case the capability of said compound of at least in part preventing the development of cardiac hypertrophy is tested. In another embodiment, HAND2 expression is induced or enhanced before said animal is provided with a candidate compound. In that case it is tested whether said compound is capable of counteracting HAND2 expression and/or activity. If cardiac muscle cell hypertrophy is already induced, the capability of a candidate compound of reducing the cardiac muscle cell size is preferably investigated.

In a preferred embodiment a non human animal according to the present invention is used in a method according to the invention. This is however not necessary: any animal expressing HAND2 or a HAND2-like compound is suitable.

The present invention allows screening of a plurality of compounds in order to search for a compound capable of counteracting and/or preventing HAND2 expression and/or activity. One embodiment provides an array of cell cultures, comprising cells according to the invention expressing HAND2 and/or HAND2-like compound. Such array allows automated screening of a plurality of candidate compounds with a method according to the invention.

Once a promising candidate compound is detected, it is preferably selected, identified and/or obtained. A method according to the invention thus preferably further comprises selecting, identifying and/or obtaining a promising candidate compound which is capable of counteracting and/or at least in part preventing cardiac hypertrophy.

A compound capable of counteracting and/or at least in part preventing cardiac hypertrophy obtainable by a method according to the present invention is also provided herewith. Since such compound is capable of at least in part preventing and/or counteracting cardiac hypertrophy, it is particularly suitable for use as a medicament. A compound according to the invention for use as a medicament and/or prophylactic agent is therefore also provided, as well as a use of a compound according to the invention for the preparation of a medicament for the treatment and/or prophylaxis of cardiac hypertrophy. Preferably a compound capable of at least in part preventing and/or counteracting cardiomyocyte hypertrophy is identified and/or obtained. Such compound is particularly suitable for use for the preparation of a disorder involved with cardiomyopathy, such as heart failure, arrhythmia, fibrotic heart disease and/or sudden death. Further provided is therefore a use of a compound according to the invention for the preparation of a medicament for the treatment and/or prophylaxis of cardiomyopathy, preferably heart failure, arrhythmia, fibrotic heart disease and/or sudden death.

One embodiment provides a compound capable of counteracting and/or at least in part preventing HAND2 expression, HAND2 activity and/or NFAT activity for use as a medicament and/or prophylactic agent. A use of a compound capable of counteracting HAND2 expression, HAND2 activity and/or NFAT activity for the preparation of a medicament for the treatment and/or prophylaxis of cardiac hypertrophy is also herewith provided. Said cardiac hypertrophy preferably involves cardiomyopathy, most preferably heart failure, arrhythmia, fibrotic heart disease and/or sudden death.

A compound according to the present invention is suitable for use in a pharmaceutical composition. One embodiment therefore provides a pharmaceutical composition comprising:

a compound obtainable by a method according to the invention, a compound capable of counteracting and/or at least in part preventing HAND2 expression, a compound capable of counteracting HAND2 activity and/or a compound capable of counteracting NFAT activity, and a pharmaceutically acceptable carrier, adjuvant, diluent and/or excipient such as for instance, but not limited to, aluminiumhydroxide.

Dose ranges of compounds according to the invention to be used in the therapeutical applications as described herein before are designed on the basis of rising dose studies in the clinic in clinical trials for which rigorous protocol requirements exist.

Further provided is a method for treatment and/or prophylaxis of cardiac hypertrophy, cardiomyopathy, heart failure, arrhythmia, fibrotic heart disease and/or sudden death, comprising administering to a subject in need thereof a therapeutically effective amount of a compound obtainable by a method according to the invention, a compound capable of counteracting and/or at least in part preventing HAND2 expression, a compound capable of counteracting HAND2 activity and/or a compound capable of counteracting NFAT activity. Administration of a pharmaceutical composition according to the present invention to a subject suffering from, or at risk of suffering from, cardiac hypertrophy, cardiomyopathy, heart failure, arrhythmia, fibrotic heart disease and/or sudden death is also herewith provided.

The invention is further explained in the following examples. These examples do not limit the scope of the invention, but merely serve to clarify the invention.

EXAMPLES

Materials and Methods

Mice. Mice expressing an activated mutant of calcineurin under control of the 5.5 kb murine cardiac a-myosin heavy chain (Myh6) promoter[1] (MHC-CnA transgenic mice) were described previously.[2] Knockout mice for Nuclear Factor of Activated T-cells isoform c2 (NFATc2) were described previously.[3] Human Hand2 with a C-terminal V5 tag was subcloned into the HindIII site downstream of a 5.5 kb murine cardiac a-myosin heavy chain (Myh6) promoter to generate the transgenic vector MHC-Hand2. Prior to oocyte injection, PvuI digestion of the MHC-Hand2 vector removed the bacterial backbone of the vector, followed by gel-purification of the transgenic construct, and injected into the pronuclei of fertilized B6CBA/F1 oocytes, which were transferred to the oviducts of pseudopregnant B6CBA/F1 recipients. Transgenic founders and progeny were identified by PCR analysis of genomic DNA using primers directed against the transgene (primer sequences available upon request). To construct the mouse Hand2 targeting vector, a targeting vector consisting of the following components is generated with the following cloning strategy: a 1.5-kb genomic fragment 5' to exon 2 (short arm); a loxP flanked 2.0 kb genomic fragment encompassing exon 2; a Frt flanked neomycin-resistance gene (neo); and a 6.0-kb genomic fragment 3' to exon 2 (long arm). The genomic fragments (short arm; exon 2; long arm) were cloned into the NotI, BamHI and SalI sites of the vector p451loxP. The linearized targeting vector was introduced into KG1 embryonic stem (ES) cells (Sv129) by electroporation and cells grown on STO feeder fibroblasts with media containing G418 and 1-(2-deoxy-2-fluoro-b-d-arabinofuranosyl)-5-iodouracil (FIAU). Drug-resistant clones were picked 10 days after selection, and targeted clones identified by Southern blot analysis of genomic DNA. Two targeted clones were obtained, and both injected into the blastocysts of C57BL 6 mice to generate chimeric mice. Chimeric offspring were bred with C57BL 6 mice to generate heterozygous targeted mice. All protocols were performed according to institutional guidelines and were approved by local Animal Care and Use Committees.

Aortic Banding. Transverse aortic banding (TAC) or sham surgery was performed in 2 month-old wildtype B6CBA and NFATc2 knockout mice by subjecting the aorta to a defined, 27 gauge constriction between the first and second truncus of the aortic arch as described previously in detail.[4] Doppler echocardiography was used to calculate the pressure gradient between the proximal and distal sites of the transverse aortic constriction using the Doppler-estimated Bernoulli's equation,[5] and only mice with a pressure gradient>20 mm Hg were included.

Transthoracic Echocardiography. Noninvasive, echocardiographic measurements were performed with a Hewlett Packard Sonos 5500 instrument (Hewlett Packard) using a 15 MHz transducer (15-6L linear probe, Philips) applied parasternally to the shaved chest wall of mice anesthetized with isoflurane as described.[6] In M-mode, the following parameters were obtained: end-diastolic LV internal diameter (LVIDd), end-systolic LV internal diameter (LVIDs); posterior wall (PW) and interventricular septum (IVS) wall thickness. Fractional shortening (FS) was calculated as (LVIDd−LVIDs)/LVIDd*100. Animals were subjected to serial, weekly echocardiographic analyses after sham operation or aortic banding for the duration of the study (4 weeks).

Cardiomyocyte cultures and siRNA transfection. Neonatal rat ventricular myocytes were obtained as described previously in detail[6]. Neonatal ventricular rat myocytes were obtained by enzymatic dissociation of 1-2 day old rat neonatal ventricles. Ventricles were stored in HEPES buffered DMEM (pH. 7.4) prior to multiple rounds of enzymatic digestion in DMEM nutrient mixture F-12 Ham base (Sigma) supplemented with 0.7 mg/ml collagenase type 2 (Invitrogen) and 1 mg/ml pancreatic (Sigma). Cells were collected by centrifugation at 61×g for 10 min., resuspended in neonatal calf serum (Invitrogen) and stored in an incubator at 37° C. All cell suspensions were pooled, centrifuged at 61×g for 10 min. and resuspended in DMEM (Invitrogen) supplemented with 10% horse serum (Invitrogen) and 5% fetal calf serum (Invitrogen). Subsequently, the cells were differentially plated for 3 hr. in uncoated cell culture dishes to remove contaminating non-myocytes. The cardiomyocytes (containing less than 5% non-myocytes) were then plated on fibronectin (Sigma)-coated 6-well culture dishes. Approximately 24 hours after plating, the media was replaced by DMEM:M199 (4:1) medium (serum free medium). For siRNA transfection, neonatal mouse cardiomyocytes were plated in DMEM supplemented with Nutridoma™ (Roche) in 12-well fibronectin-coated plates with density of 4*10⁵ cells per well and transfected the next day with 100 nM of siRNA duplex (Ambion) specific for GFP ('scrambled siRNA' 5'-AAC-GAUGCCACCUACGGCAAGdTdT-3') (SEQ ID NO:1) or a duplex specific for murine HAND2 in 2 ml. oligofectamine (Invitrogen). Cells were washed the next day and incubated for another 48 hours before treatment.

Chromatin immunoprecipitation. Hearts from wildtype and MHC-CnA transgenic mice were perfusion fixed with 1% formaldehyde. Ventricular tissue was dounce-homogenized and sonicated to obtain soluble chromatin. Chromatin immunoprecipitation was carried out using the Upstate Biotechnology ChIP assay kit according to manufacturer's instructions using the following antisera: anti-acetylated histone H3 antibody (Upstate), and antisera against NFATc3 (Santa Cruz). Equal amounts of soluble chromatin from each sample were immunoprecipitated with 1 mg of the abovementioned antibodies. Following immunoprecipitation and immobilization of immunocomplexes, reverse crosslinking was obtained by incubation at 65° C. for 4 hours. Associated DNA was purified by phenol/chloroform extraction and PCR is carried out using specific primers to the promoter region of the mouse hand2 gene.

Histological Analysis. Hearts are arrested in diastole and perfusion fixed with 4% paraformaldehyde and embedded in paraffin. Sections (6 mm) are cut and stained with hematoxylin and eosin (H&E).

Recombinant adenoviruses. C-terminal V5-tagged human Hand2 encompassing residues 1-216 was cloned into the pDC516 viral shuttle vector[7] to generate AdHand2. AdGFP was generated as described previously.[8] An adenovirus expressing an activated mutant of calcineurin (AdCnA) was described earlier.[6]

Cell culture, transient transfections and luciferase assays. Isolation and culture of neonatal rat ventricular cardiomyocytes was performed as described before in detail.[9] Transient transfections were performed as described[9] with FuGENE 6 reagent as per the manufacturer's recommendations.

Generation of stable cardiac cell lines. HEK293 and human cardiac progenitor cells were cultured as described previously.[10] Double stable, Hand2-inducible cells were generated using the T-REX system (Invitrogen) with modifications. Briefly, cells were transfected using FUGENE 6 reagent (Roche) with 8 µg pCAgβTrs-hygro, a vector expressing the Tet-repressor (TR) under control of a β-actin promoter (generously provided by Hans Clevers, The Hubrecht Institute) and stable clones selected with 250 µg/µl hygromycin. Selected colonies were transiently transfected using FUGENE 6 reagent (Roche) with 0.2 µg pcDNA4/TO-luciferase (Invitrogen) to test their responsiveness to doxycyclin (Dox) using the Dual Luciferase assay system (Promega). Two different Tet-repressor clones (TR1 and TR4), showing high luciferase activity and low background, were subsequently transfected with 8.5 µg pcDNA4/TO-Hand2 using FUGENE 6 reagent (Roche) and cultured in the presence of hygromycin and 750 µg/µl zeocin to generate double stable cell lines. Zeocin/hygromycin resistant clones were transiently transfected with a reporter construct encoding firefly luciferase under control of the proximal promoter region of the rat ANF gene (base pairs −3003 to +1 relative to the beginning of exon 1) to test their DOX-inducible Hand2 transcriptional activation profile.

Primary high throughput screen (HTS). TR-Hand2 cells were cultured in DMEM with 10% (vol/vol) FBS/4 mM L-glutamine/1% penicillin/streptomycin. Cells at a concentration of 50,000 cells per ml were transiently transfected in batch with a reporter construct (20 pg per cell) encoding firefly luciferase under control of the proximal promoter region of the rat ANF gene (base pairs −3003 to +1 relative to the beginning of exon 1) or a reporter construct encoding firefly luciferase under control of the CMV promoter and FuGENE transfection reagent. Transfected cells were plated on 96-well plates (Packard) at a density of 5,000 cells per well. A 10,000 member library of small molecule test compounds from the Lead Pharma Library (Selected on Lead-likeness and molecular diversity from the global supplier database of Pyxis Delft the Netherlands) were then added by using a robotic liquid handling system (one compound per well, 10 µM concentration).

Northern blot analysis. Northern blot analysis for Hand2 was performed with 20 µg of total RNA in each lane and probed in Ultrahyb (Ambion, Austin, Tex.) with a $^{32}$P-labeled DNA fragment encompassing the full-length human transcript for Hand2 (Radprime, Invitrogen). Signals were detected using a phosphor imaging screen (Biorad) and images visualized in Adobe Photoshop software (Adobe).

Western Blot Analysis. SDS PAGE electrophoresis and blotting was performed as described in detail.[9] Antibodies used included monoclonal anti-GFP (Santa Cruz, 1:500), polyclonal rabbit anti-Hand2 (Santa Cruz; 1:500), and monoclonal anti-V5 (Sigma, 1:5000), followed by corresponding horseradish peroxidase (HRP)-conjugated secondary antibodies (DAKO, 1:5000) and ECL detection.

Immunocytochemistry and confocal microscopy. To visualize cardiomyocyte size and sarcomeric organization, cultured cardiomyocytes were fixed for 10 min in 4% paraformaldehyde and permeabilized with 0.2% Triton X-100 in PBS for 5 minutes. Primary and secondary antibodies were diluted using 1% BSA in TBS and incubations were carried out at room temperature for 1 hour. Cells were washed 3 times with PBS for 5 minutes, mounted with coverslips in 0.1 M Tris-HCl (pH 9.5)-glycerol (3:7) including 50 mg/ml n-propylgallate as anti-fading reagent, and analyzed by confocal microscopy using a Zeiss LSM 510 META instrument. Antibodies used included mouse anti a-actinin (Sigma, 1:500); Cy5 goat anti-rabbit and Cy3 goat anti-mouse (Jackson Immuno Research, 1:100 and 1:500, respectively); TOPRO-3 (1:100). Cell surface areas were determined using SPOT-imaging software (Diagnostic Instruments) on 80-100 GFP-positive cardiomyocytes in 10 to 20 fields in three independent experiments.

Agilent Gene Expression Profiling and Data Analysis. Total RNA was extracted from three hearts of each experimental groups using Trizol (Invitrogen) and cleaned with Qiagen RNeasy Mini Kits (Qiagen). RNA quantity from the individual hearts was measured with a NanoDrop® ND-1000 UV-Vis Spectrophotometer (Wilmington), and RNA quality was monitored using an Agilent 2100 bioanalyzer. Agilent 22k mouse genome microarray slides were used and a dye-swap experimental design applied. RNA samples from individual hearts within one group was pooled and RNA samples from the experimental groups (500 ng each) were amplified and labeled with Cy5- and Cy3-CTP (Perkin Elmer) to produce labeled cRNA using Agilent low RNA input fluorescent linear amplification kits following the manufacturers protocol. After amplification and labeling, the dye-incorporation ratio was determined with NanoDrop® ND-1000 UV-V is Spectrophotometer (Wilmington). For hybridization, the guidelines for 22k format arrays with cRNA targets were strictly followed. Briefly, 750 ng of Cy3-labeled cRNA and 750 ng Cy5-labeled cRNA were mixed and incubated with an Agilent microarray slide for 17 hours using an Agilent in situ hybridization kit following SSC buffer washing. The washed slides were immediately dried, and scanned using Agilent DNA Microarray Scanner (G2565BA). Raw data were generated using Agilent's Feature Extraction software (FE v7.1). Gene classifications were assigned based upon publicly available software and websites, including FATIGO Data mining with Ontology (www.fatigo.org), Mouse Genome Informatics (MGS; www.informatics.jax.org), GenBank and Medline.

Real Time PCR and Primer Design

Primers were targeted against transcripts for mouse atrial natriuretic factor (ANF or nppa), brain natriuretic peptide (BNP or nppb), b-myosin heavy chain (b-MHC or myh7), Hand2, and L7. The primers were specific for mouse sequences (www.ensembl.org) and selected using Beacon Designer software (Invitrogen) based on the following requirements: i) primer melting temperature of ~60° C., ii) GC-content of ~55%, iii) preferably no G at 5' end, iv) avoid runs of more than 3 identical nucleotides, and v) amplicon length of ~100 nucleotides. Specificity was checked with the Basic Local Alignment Search Tool (BLAST) and the specific melting point of the amplicons was analyzed using Biorad Dissociation curve software (iCycler, Biorad). All primer sets were tested for PCR efficiency and alternative primers were designed in case they fell outside the 5% efficiency range ($3.14 \leq slope \leq 3.47$).

Three μg of RNA from indicated hearts was reverse-transcribed using Superscript II reverse transcriptase (Invitrogen). Real-time PCR using the BioRad iCycler (Biorad) and fluorescence detection was performed in 96-well plates using SYBR Green. PCR amplification was performed (in duplicate) as a singleplex reaction in a total reaction volume of 25 μl, consisting of 400 nM forward and reverse primers, 40 ng cDNA, 12.5 μl 2×SYBR Green PCR master mix (Biorad). The PCR was cycled between 95° C./30 s and 60° C./30 for 40 cycles, following an initial denaturation step at 95° C. for 3 min. Transcript quantities were compared using the relative $C_t$ method, where the amount of target normalised to the amount of endogenous control (L7) and relative to the control sample is given by $2^{-DDCt}$. Real time PCR results were verified by electrophoresis of the reverse transcribed material in 1.2% agarose gels and visualized under UV illumination after ethidium bromide staining. Primer sequences are available upon request.

Statistical analysis. The results are presented as mean values±standard error of the mean (SEM). Statistical analyses were performed using SPSS and InStat 3.0 software (GraphPad Software Inc.) and consisted of ANOVA followed by Tukey's post-test when group differences were detected at the 5% significance level, or Student's T-test when comparing two experimental groups.

Results

Gene expression profiling of calcineurin transgenic mice either or not intercrossed with NFATc2 knockout mice. We analyzed whether NFAT transcriptional activity underlies the cardiomyopathic response in mice harboring a heart-restricted transgene encompassing an activated mutant of calcineurin (MHC-CnA TG mice), by crossbreeding with mice lacking a major cardiac NFAT isoform, NFATc2 (NFATc2 knockout mice). Heart size of wildtype mice was indistinguishable from NFATc2 knockout mice (FIG. 1a). In line with previous findings,[2, 6] MHC-CnA mice displayed a three-fold increase in heart size with severe biventricular dilation at four weeks of age. Remarkably, once MHC-CnA mice were crossbred with NFATc2 knockout mice, gross cardiac morphology analysis indicated reduced heart weight (FIG. 1a). These data indicate that the NFATc2 transcription factor isoform plays a decisive role downstream of calcineurin signaling in the adult heart.

HAND2 is a direct cardiac target gene of cardiac calcineurin/NFAT signaling. To provide more insights into the mechanisms underlying the phenotypic rescue evoked by inhibition of NFAT transcriptional activity downstream of calcineurin in the heart, we analyzed the relative gene expression profiles from the indicated experimental groups with Agilent mouse chips containing 22,000 genes. One gene that demonstrated opposite expression in MHC-CnA mice compared MHC-CnA/NFATc2 KO mice was the class II basic helix-loop-helix (bHLH) transcription factor heart and neural crest derived 2 or hand2 (FIG. 2b). The differential expression of hand2 transcripts by microarray profiling was confirmed by real time RT-PCR (FIG. 2c). HAND1 and HAND2 are related basic helix-loop-helix (bHLH) transcription factors that are expressed in mesodermal and neural crest-derived structures of the developing heart. During mouse heart development HAND1 and HAND2 are expressed in a complementary fashion and are restricted to segments of the heart tube fated to form the left and right ventricles, respectively. HAND1 and HAND2 represent the earliest cardiac chamber-specific transcription factors yet identified. Targeted gene deletion of HAND2 in mouse embryos resulted in embryonic lethality at embryonic day 10.5 from defects in neural crest and ventricular morphogenesis.[10] Given that no information is available about HAND2 expression in adult mammalian tissues, we examined HAND2 transcript abundance in normal tissues using Northern blot analysis. The data indicate that HAND2 is solely expressed at a very low level in the adult brain and heart (FIG. 2d). Combined, these data indicate that HAND2 expression is expressed at very low levels in the normal adult myocardium, and induced by cardiac calcineurin/NFAT signaling in the adult heart.

Biomechanical stress induces HAND2 expression. Biomechanical stress activates signaling cascades including oxidative stress[11], predisposes cardiac muscle to late-onset apoptosis[4, 12-14], and provokes progressive left ventricular remodeling and heart failure[12, 13]. Transverse aortic constriction is a surgical procedure that mimics human disorders such as chronic hypertension or aortic valve stenosis. First, we verified whether our transverse aortic constriction (TAC) procedure (FIG. 2a) provoked an equal transtenotic pressure gradient in both wildtype and NFATc2 knockout mice. The data demonstrate that equal loading was imposed on the left ventricle of both genotypes subjected to TAC compared to sham operated animals (FIG. 2b). Next, we analyzed heart weight to body weight ratios for the 4 experimental cohorts and found an approximate 40% increase in corrected heart weight (hypertrophy) in wildtype mice at 1 week after TAC. In contrast, at 1 week after TAC, NFATc2 knockout mice only 10% cardiac hypertrophy (FIG. 2c). These data indicate that NFATc2 knockout mice are not only protected against cardiac hypertrophy in response to an activated calcineurin transgene, but also are resistant to pressure overload-induced hypertrophy.

Next, we analyzed the expression of cardiac hypertrophy marker gene expression in the four experimental cohorts, including transcript abundance of classical hypertrophy marker genes such as ANF, BNP and b-MHC by RT-PCR (FIG. 2d) and real time PCR (FIG. 2e). The marker genes demonstrated robust increase in expression in wildtype mice subjected to TAC compared to sham operated wildtype mice. Sham operated NFATc2 knockout mice displayed low expression of the classical hypertrophy markers, and, in line with the data in FIG. 2c, demonstrated a profound inhibition of marker gene expression after 1 week of TAC. Interestingly, HAND2 transcript abundance behaved as the classical hypertrophy markers tested in our analyses, its expression was very low in sham operated mice, induced in TAC subjected wildtype mice, and its expression was substantially blunted in TAC subjected NFATc2 knockout mice. These data indicate that HAND2 expression is specifically induced by NFATc2 transcriptional activity in the heart in response to biomechanical stress.

Increased HAND2 expression in human heart failure secondary to chronic aortic stenosis. To explore whether increased HAND2 transcript abundance also translates into increased protein levels and whether or not this represents a phenomenon restricted to animal models or also relates to human heart disease, we performed a series of Western blot analyses for HAND2 in biopsies from human control hearts and explanted human failing hearts secondary to chronic aortic stenosis. The data indicate that HAND2 protein expression was low to absent in control hearts, while in human failing hearts HAND2 expression was substantially increased (FIG. 3a, b). These data show that HAND2 is increased in human failing hearts.

Activation of HAND2 induces hypertrophy in cultured cardiomyocytes To address the role of HAND2 in cardiomyocyte remodeling, we generated an adenoviral vector to overexpress HAND2. A replication-deficient adenovirus was generated expressing both human HAND2 fusion protein expressing the V5/His tag at the C-terminal end under control of a CMV promoter (FIG. 4a). Western blotting with anti-V5 and anti-GAPDH antibodies confirmed that the virus expressed a protein of the correct size (FIG. 4b). The virus was then used to infect cultured neonatal rat ventricular myocytes. Following infection, cells were serum starved for 48 h, fixed and stained for α-actinin to identify cardiomyocytes and visualize myofibrils, and counterstained with TOPRO-3 to visualize nuclei (FIG. 4c). Control cells (AdLacZ infected) showed no signs of hypertrophy. As expected, cardiomyocytes infected with AdHAND2 demonstrated a clear hypertrophic phenotype. In line, AdHAND2-infected cultures revealed a significant increase in average cell surface area, a measure of hypertrophy, as compared to AdLacZ-infected cultures (FIG. 4d). Combined, these data demonstrate that an increase in HAND2 transcriptional activity in cultured cardiomyocytes, accomplished by AdHAND2 infection, provokes a classical hypertrophic response in cardiomyocytes.

Increased HAND2 expression induces the ANF hypertrophic marker gene. To explore whether increased HAND2 expression translates into its ability to induce the expression of downstream target genes in a series of transient cotransfection assays. Cotransfection of (−3003)ANF-Luc with expression vectors for HAND2 and the uniquitous class I bHLH transcription factor E12, increased the induction of the ANF reporter several-fold (FIG. 4e). Taken together, these results indicate that ANF is a direct target gene for HAND2, and suggests that increased HAND2 expression provokes a hypertrophic gene program.

Transgenic overexpression of HAND2 in the heart muscle suffices to provoke cardiac hypertyrophy. To verify whether HAND2 transcriptional function in vivo would also translate into cardiac enlargement, we designed a strategy to activate HAND2 transcriptional activity in the postnatal heart. We generated transgenic mice expressing HAND2 under control of the well-characterized 5.5 kb murine a-myosin heavy chain (Myh6) promoter (FIG. 4f). Eight independent founders were recovered, all which produced progeny and established transgenic lines for further characterization. All viable HAND2 transgenic lines overexpressed human HAND2 in the myocardium, albeit at differing levels, varying between 1.5-5 fold more HAND2 protein at 12 weeks of age, when normalized to GAPDH (data not shown). One high expressor line was characterized by substantial enlargement of both right and left ventricular chambers at 12-weeks of age, and severely thinned ventricular walls (FIG. 4g and data not shown). Combined, these data show that cardiac HAND2 activation produces a dose-dependent, variable phenotype ranging from no apparent phenotype, slight hypertrophic/dilated remodeling, and severe dilated cardiomyopathy characterized by ballooning of the ventricular chambers and thinning of ventricular walls.

Inhibition of HAND2 reduces cardiomyocyte hypertrophy. To begin to assess the requirement of HAND2 downstream of (calcineurin-mediated) cardiomyocyte hypertrophy, we designed specific short hairpins targeted against endogenous HAND2 in cardiomyocytes, and transfected the HAND2 siRNA into cell cultures. As a control, we also transfected a non-specific control siRNA in cardiomyocytes (FIG. 5a). We selected one siRNA species that very efficiently knocked-down HAND2 protein expression as measured by Western blotting with an antibody targeting the C-terminal V5-epitope (FIG. 5a). To investigate the requirement of HAND2 in calcineurin-mediated cardiomyocyte hypertrophy, we infected cardiomyocyte cultures, pretreated with either HAND2 specific siRNAs or control siRNAs, with an adenovirus expressing an activated form of calcineurin (AdCnA), or exposed to 10 mM phenylephrine (PE). To monitor the change in cell size or sarcomere organization, cardiomyocytes were stained for sarcomeric a-actinin. AdCnA or PE treatment resulted in robust hypertrophy response when cells were treated with the control siRNA. In contrast, pretreatment with the siRNA against HAND2 completely abrogated the classical hypertrophy response in response to AdCnA-infection or PE treatment. In line, quantification of the data indicated an almost 2-fold increase in cell surface area in AdCnA-infected cells pretreated with the control siRNA. In contrast, pretreatment with the HAND2 selective siRNA abrogated the prohypertrophic effects of AdCnA. The data demonstrate that HAND2 mediates the hypertrophic remodeling of cardiomyocytes following calcineurin activation.

In summary, the present study provides the first direct approach to study the biological ramifications of the transcription factor HAND2 in the postnatal heart muscle. Our findings demonstrate that HAND2 expression is low in the normal postnatal myocardium and strongly re-induced upon pathological signals including chronic calcineurin activation, pressure overload or aortic stenosis in several animal species (mouse, rat, human), strongly suggesting a species conserved mechanism. More importantly, HAND2 is able to activate the ANF and BNP genes in postnatal myocardial tissue, which are widely used as biomarkers for pathological hypertrophy and heart failure. Increased HAND2 expression suffices to provoke cardiomyocyte hypertrophy in cell culture and in vivo using transgenic techniques. Finally, HAND2 seems to be a required component of pathological hypertrophy, since siRNA-mediated knock-down of HAND2 crippled primary cardiomyocytes to induce a hypertrophy response secondary to calcineurin activation or phenylephrine stimulation. The combined findings show that HAND2 promotes multiple cellular changes, each of which may independently or in an interconnected fashion promote changes of the heart muscle that are characteristic of cardiac hypertrophy and heart failure.

REFERENCES

Figure 1:
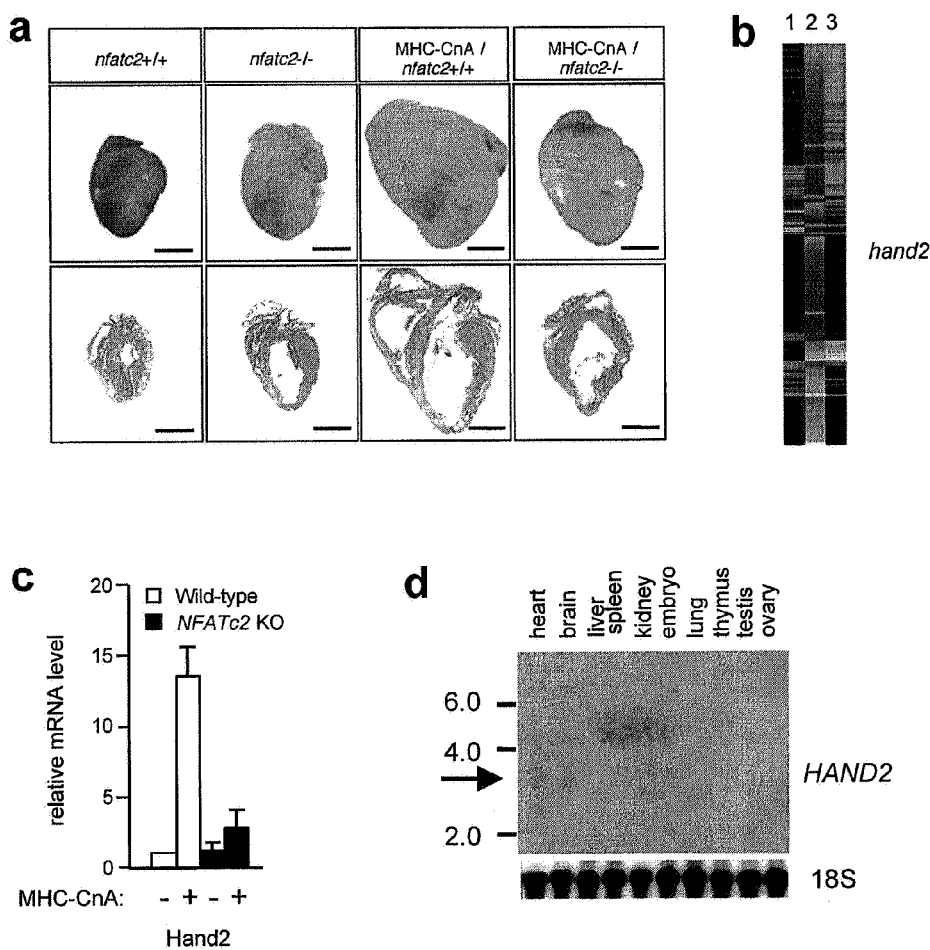
FIG. 1. Gravimetrical, histological, and molecular analysis of calcineurin-transgenic mice crossed into an nfatc2-null background. (a) Representative gross morphology and H&E-stained four-chamber view of hearts dissected from 3 week-old mice of indicated genotypes, demonstrating a profound rescue of cardiac enlargement by nfatc2 ablation downstream of calcineurin activation (bar 5 mm). (b) Heat map representation of microarray analyses performed on wildtype mice (1), MHC-CnA transgenic mice (2), and MHC-CnA mice with an nfatc2-deficient background (3). The relative position of the gene hand2 is indicated. (c) Real time RT-PCR quantification of hand2 transcript abundance in indicated genotypes confirms a dramatic induction in hand2 transcripts in hearts from MHC-can transgenic mice, and a substantial attenuation of this induction in MHC-CnA mice with an nfatc2-deficient background. (d) Northern blot analysis on total RNA isolated from several human tissues using a radioactive probe against human hand2 transcripts, indicates a very low signal in heart and brain.
Figure 2:
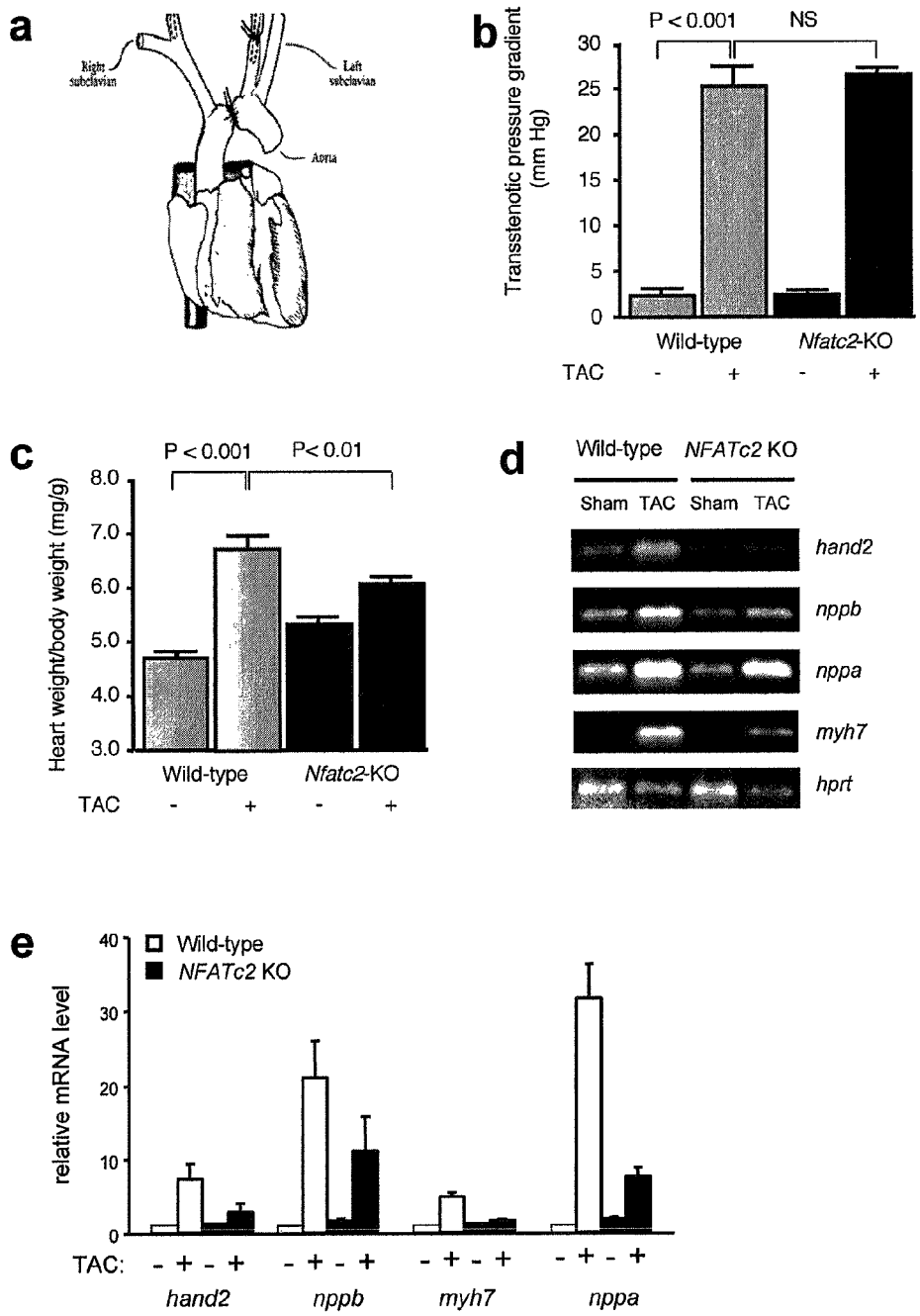
FIG. 2. Nfatc2 ablation prevents pressure overload induced cardiac hypertrophy and hand2 mRNA induction. (a) Schematic representation of the transverse aortic constriction method, indicating the site of partial ligation of the transverse aorta. (b) Pressure gradients across the proximal and distal transverse aorta were measured noninvasively to validate the TAC procedure. (c) Heart weight to body weight (HW/BW) ratios of indicated genotypes subjected to sham or TAC surgery show a decreased hypertrophic response for nfatc2−/− hearts compared to wild type hearts after one week of TAC. (d) RT-PCR analysis of several transcripts, including hand2, and the cardiac hypertrophy marker genes nppa, nppb, and myh7. Transcript abundance of hypoxanthine phosphoribosyltransferase (hprt) was used as a loading control. (e) Real time RT-PCR quantification of hand2, nppa, nppb and myh7 transcript abundance in wildtype and nfatc2 knockout mice subjected to sham or TAC surgery confirms a dramatic induction in hand2 transcripts in hearts from wildtype mice, and a substantial attenuation of this induction in nfatc2 knockout mice. These data confirm that hand2 mRNA induction is dependent upon NFAT transcriptional activity in the hypertrophic heart.
Figure 3:
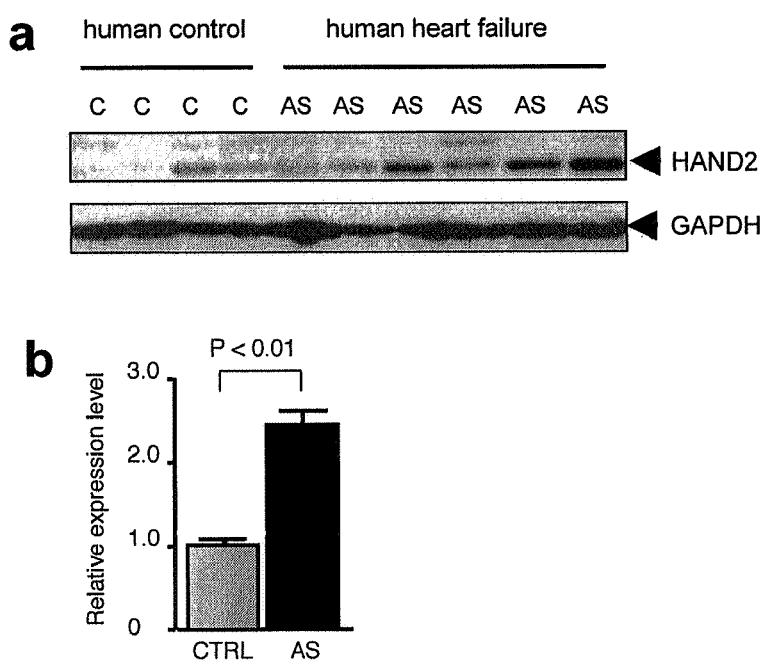
FIG. 3. Hand2 protein induction in human heart failure hearts. (a) Western blot analysis of Hand2 protein abundance in left ventricular biopsies from control human hearts (C), and left ventricular biopsies derived from human heart failure patients due to aortic stenosis (AS) (upper panel). As a loading control the same membrane was stripped and reprobed with an antibody against GAPDH (lower panel). The data show some variability between patients in Hand2 protein abundance, but overall in control patients, hand2 protein abundance was relatively low, while in human heart failure hearts hand2 protein abundance was relatively higher. (b) Quantification of the average western blot signals for hand2 protein abundance corrected for loading controls show an average 2.3-fold increase in failing human hearts.
Figure 4:
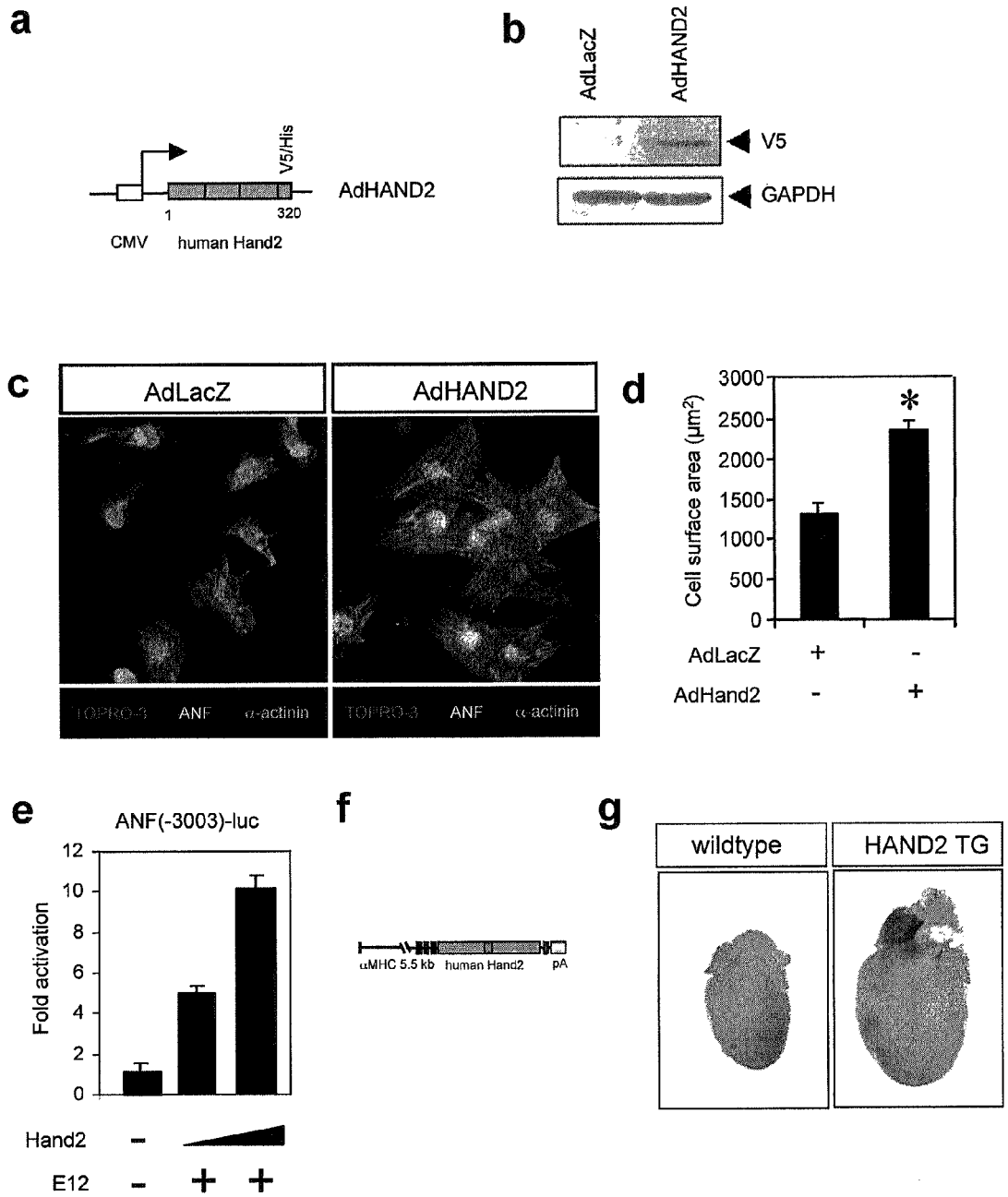
FIG. 4. Forced overexpression of hand2 provokes cardiomyocyte hypertrophy in vitro and cardiac enlargement in vivo. (a) Schematic representation of an adenoviral vector designed to overexpress human Hand2 harboring a C-terminal V5/His tag under control of a CMV promoter. (b) Western blot analysis of cardiomyocytes infected with a control adenovirus expressing b-galactosidase (AdLacZ) or Hand2 (AdHand2). The presence of Hand2 with a V5 epitope was readily detected (upper panel), loading control was performed with an antibody against GAPDH. (c) Representative confocal image of neonatal rat cardiomyocytes infected with a control adenovirus or AdHand2 and stained for a-actinin, ANF and a nuclear counterstain (TOPRO-3). The data show dramatically enlarged cardiomyocytes with induction of perinuclear ANF upon overexpression of Hand2. (d) Quantification of cell surface areas of indicated conditions confirms the enlargement of individual cardiomyocytes upon Hand2 overexpression. (e) Transient transfection assay using a reporter construct encoding firefly luciferase under control of the proximal promoter region of the rat ANF gene (base pairs −3003 to +1 relative to the beginning of exon 1) to verify whether Hand2 can induce expression of ANF. The data demonstrate that Hand2 is able to dose-dependently activate the ANF reporter gene in the presence of the ubiquitously expressed E12 bHLH factor. (f) Schematic representation of the transgenic vector designed to overexpress Hand2 in postnatal cardiac muscle in transgenic mice. (g) Representative image of hearts isolated from 6-week old wildtype and transgenic littermates, indicating that postnatal overexpression of Hand2 (MHC-Hand2) suffices to provoke cardiac hypertrophy in vivo.
Figure 5:
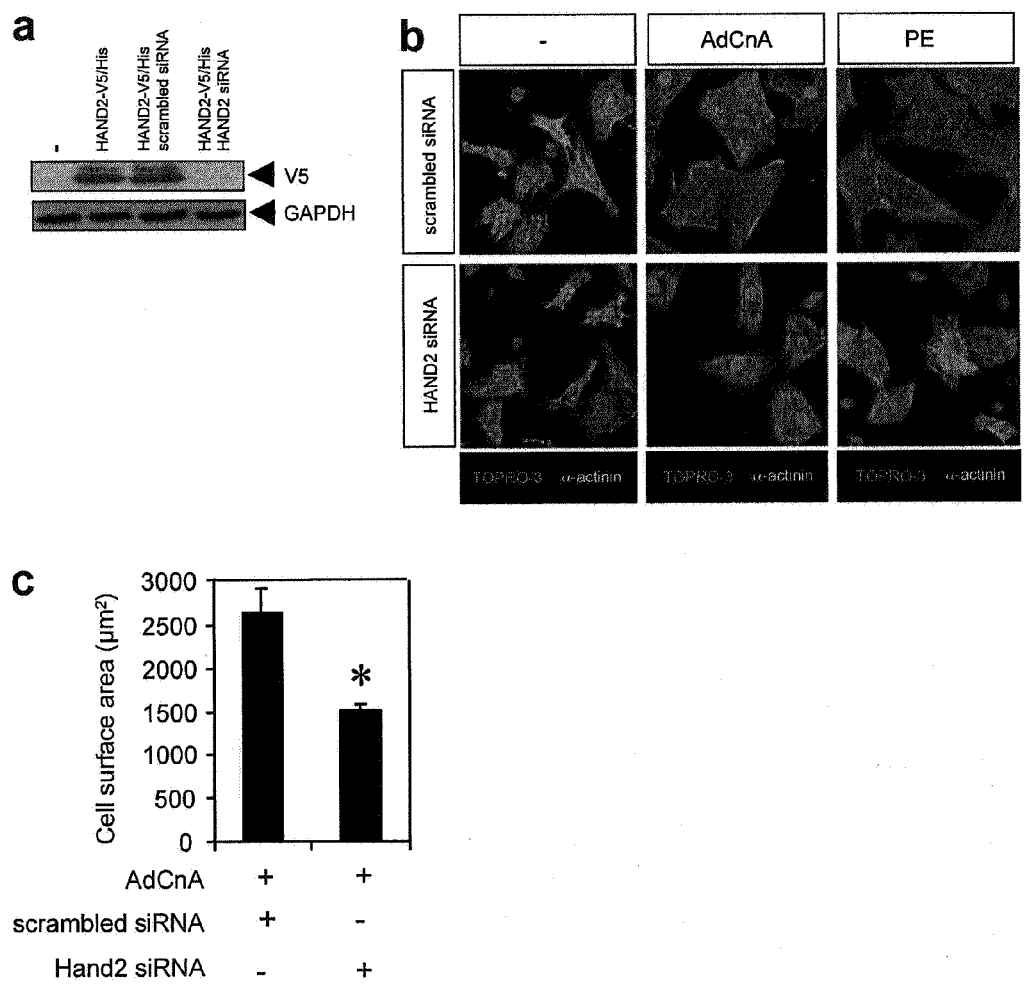
FIG. 5. Hand2 knockdown prevents cardiomyocyte hypertrophy in response to pro-hypertrophic stimuli. (a) Western blot analysis showing that a short hairpin designed to knock down Hand2 prevents protein expression of a C-terminally V5-tagged form of Hand2 at the protein level. (b) Neonatal rat cardiomyocytes were either transfected with a non-specific siRNA (scrambled siRNA) or a siRNA against Hand2. Twenty-four hrs later, cells were left untreated, or infected with an adenovirus expressing a constitutively activated form of calcineurin, or treated with 10 mM phenylephrine. The data show that a siRNA against Hand2 largely prevents cardiomyocyte hypertrophy secondary to calcineurin signaling or phenoylephrine stimulation. (c) Quantification of the conditions depicted in panel (b).
Figure 6:
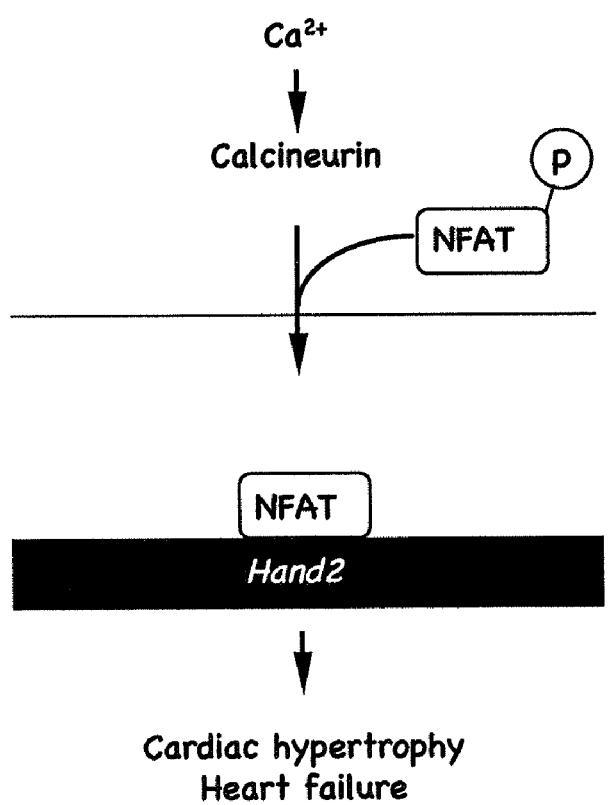
FIG. 6. Hand2 functions downstream of calcineurin/NFAT signaling in cardiac hypertrophy and heart failure. Following cardiac calcineurin activation, Hand2 is induced by NFAT transcriptional activity, provoking cardiac hypertrophy and heart failure.

1. Palermo J, Gulick J, Colbert M, Fewell J, Robbins J. Transgenic remodeling of the contractile apparatus in the mammalian heart. *Circ Res*. March 1996; 78(3):504-509.
2. Molkentin J D, Lu J R, Antos C L, Markham B, Richardson J, Robbins J. Grant S R, Olson E N. A calcineurin-dependent transcriptional pathway for cardiac hypertrophy. *Cell*. 1998; 93(2):215-228.
3. Ranger A M, Gerstenfeld L C, Wang J, Kon T, Bae H, Gravallese E M, Glimcher M J, Glimcher L H. The nuclear factor of activated T cells (NFAT) transcription factor NFATp (NFATc2) is a repressor of chondrogenesis. *J Exp Med*. Jan. 3, 2000; 191(1):9-22.
4. van Empel V P, Bertrand A T, van der Nagel R, Kostin S, Doevendans P A, Crijns H J, de Wit E, Sluiter W, Ackerman S L, De Windt L J. Downregulation of apoptosis-inducing factor in harlequin mutant mice sensitizes the myocardium to oxidative stress-related cell death and pressure overload-induced decompensation. *Circ Res*. Jun. 24, 2005; 96(12): e92-e101.
5. Schultz J E, Witt S A, Nieman M L, Reiser P J, Engle S J, Zhou M, Pawlowski S A, Lorenz J N, Kimball T R, Doetschman T. Fibroblast growth factor-2 mediates pressure-induced hypertrophic response. *J Clin Invest*. September 1999; 104(6):709-719.
6. De Windt L J, Lim H W, Taigen T, Wencker D, Condorelli G, Dorn G W, 2nd, Kitsis R N, Molkentin J D. Calcineurin-mediated hypertrophy protects cardiomyocytes from apoptosis in vitro and in vivo: An apoptosis-independent model of dilated heart failure. *Circ Res*. 2000; 86(3):255-263.

7. He T C, Zhou S, da Costa L T, Yu J, Kinzler K W, Vogelstein B. A simplified system for generating recombinant adenoviruses. *Proc Natl Acad Sci USA*. Mar. 3, 1998; 95(5): 2509-2514.
8. Ng P, Cummings D T, Evelegh C M, Graham F L. Yeast recombinase FLP functions effectively in human cells for construction of adenovirus vectors. *Biotechniques*. September 2000; 29(3):524-526, 528.
9. van Rooij E, Doevendans P A, de Theije C C, Babiker F A, Molkentin J D, de Windt L J. Requirement of nuclear factor of activated T-cells in calcineurin-mediated cardiomyocyte hypertrophy. *J Biol Chem*. Dec. 13, 2002; 277(50):48617-48626.
10. Srivastava D, Thomas T, Lin Q, Kirby M L, Brown D, Olson E N. Regulation of cardiac mesodermal and neural crest development by the bHLH transcription factor, dHAND. *Nat Genet*. June 1997; 16(2):154-160.
11. Lorell B H, Carabello B A. Left ventricular hypertrophy: pathogenesis, detection, and prognosis. *Circulation*. Aug. 25, 2000; 102(4):470-479.
12. Hirota H, Chen J, Betz U A, Rajewsky K, Gu Y, Ross J, Jr., Muller W, Chien K R. Loss of a gp130 cardiac muscle cell survival pathway is a critical event in the onset of heart failure during biomechanical stress. *Cell*. Apr. 16, 1999; 97(2):189-198.
13. Zhang D, Gaussin V, Taffet G E, Belaguli N S, Yamada M, Schwartz R J, Michael L H, Overbeek P A, Schneider M D. TAK1 is activated in the myocardium after pressure overload and is sufficient to provoke heart failure in transgenic mice. *Nat Med*. May 2000; 6(5):556-563.
14. Sadoshima J, Montagne O, Wang Q, Yang G, Warden J, Liu J, Takagi G, Karoor V, Hong C, Johnson G L, Vatner D E, Vatner S F. The MEKK1-JNK pathway plays a protective role in pressure overload but does not mediate cardiac hypertrophy. *J Clin Invest*. July 2002; 110(2):271-279.

determining whether expression and/or activity of said HAND2 by said cell is lower than expression and/or activity of said HAND2 by the same kind of cell cultured in the absence of said candidate compound; and determining that a candidate compound is capable of counteracting cardiac hypertrophy if said candidate compound lowers the expression and/or activity of said HAND2 or determining that a candidate compound is not capable of counteracting cardiac hypertrophy if said candidate compound does not lower the expression and/or activity of said HAND2.

2. A method according to claim 1, wherein said determining comprises assessing whether the size of the cell cultured in the presence of said candidate compound is smaller than the size of the same kind of cell cultured in the absence of said candidate compound.

3. A method according to claim 1, wherein the HAND2 expressing cell is a cardiomyocyte which exhibits cell hypertrophy in the absence of said candidate compound and wherein said determining comprises assessing whether the size of said cardiomyocyte reduces over time.

4. A method according to claim 1, wherein said cell is a cell wherein expression, and/or activity of HAND2 is increased as compared to the same kind of cell in its natural environment.

5. A method according to claim 3, wherein said cell is present in a non human animal and said method comprises providing said candidate compound to said non human animal.

6. A method according to claim 5, wherein said non human animal comprises a cell wherein expression, and/or activity of HAND2 or a functional part or derivative thereof, and/or

The invention claimed is:

1. A method for determining whether a candidate compound is capable of counteracting cardiac hypertrophy, comprising:

culturing a heart and neural crest derived 2 transcription factor (HAND2) expressing cell in the presence of said candidate compound; and HAND2-like compound is increased as compared to the same kind of cell in its natural environment.

7. A method according to claim 1, wherein a plurality of candidate compounds is tested.

8. The method of claim 1 wherein said determining is conducted after at least 12 hours of said culturing.

* * * * *

UNITED STATES PATENT AND TRADEMARK OFFICE
CERTIFICATE OF CORRECTION

PATENT NO.        : 8,367,342 B2
APPLICATION NO.   : 12/520516
DATED             : February 5, 2013
INVENTOR(S)       : Da Costa Martins et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 688 days.

Signed and Sealed this
First Day of September, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 23
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: 22, 23
<223> OTHER INFORMATION: t = dihydrothymine

<400> SEQUENCE: 1
aacgaugcca ccuacggcaa gtt                                            23
```